United States Patent [19]
Kim et al.

[11] Patent Number: 6,041,251
[45] Date of Patent: Mar. 21, 2000

[54] SYSTEM AND METHOD FOR DETECTING ATRIAL EVENTS OF A HEART

[75] Inventors: Jaeho Kim, Redmond; Joseph M. Bocek, Seattle, both of Wash.

[73] Assignee: Cardiac Pacemakers, Inc., Minneapolis, Minn.

[21] Appl. No.: 09/108,898

[22] Filed: Jul. 1, 1998

[51] Int. Cl.[7] .................................................. A61B 5/046
[52] U.S. Cl. ............................................... 600/518; 607/5
[58] Field of Search ........................... 607/4, 5; 600/515, 600/518, 521

[56] References Cited

U.S. PATENT DOCUMENTS 5,267,559  12/1993  Jin et al. ........................................ 607/5
5,685,315  11/1997  McClure et al. ........................ 600/521

*Primary Examiner*—Jeffrey R. Jastrzab
*Attorney, Agent, or Firm*—Foley & Lardner

[57] ABSTRACT

A continuous monitoring system monitors atrial activity of a heart and activates an atrial fibrillation detector when atrial fibrillation is suspected. The system includes an A wave detector for detecting A waves of the heart and providing an A wave detection signal indicating each detected A wave. The A wave detector has a first threshold and a selectable second threshold higher than the first threshold. An R wave detector for detecting R waves of the heart is coupled to the A wave detector for selecting the second threshold of the A wave detector during each detected R wave of the heart. An atrial cycle length determining stage determines atrial cycle lengths from the A wave detection signal and a comparator activates atrial fibrillation detection when an atrial cycle length is shorter than a predetermined cycle length.

9 Claims, 1 Drawing Sheet

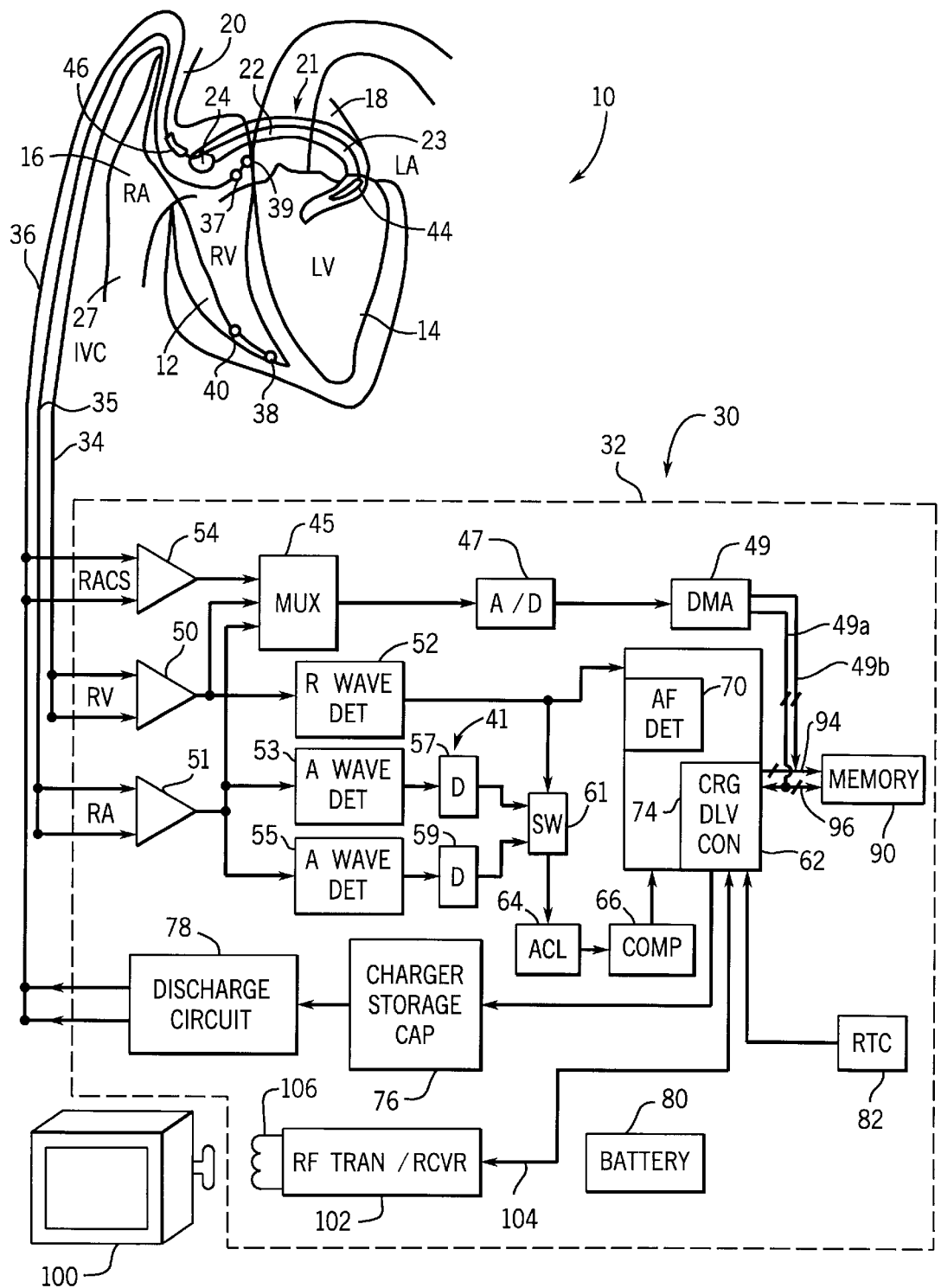

SYSTEM AND METHOD FOR DETECTING ATRIAL EVENTS OF A HEART

BACKGROUND OF THE INVENTION

The present invention generally relates to a method and system for detecting atrial events of a heart. The present invention is more particularly directed to such a system and method which detects A waves of a heart in the presence of ventricular activity wherein A waves are normally detected with a first threshold but, during detected ventricular activity the threshold is raised to a second threshold, higher than the first threshold to avoid sensing ventricular activity as atrial activity.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience rapid and irregular beating of the heart and may even experience dizziness as a result of reduced cardiac output.

Atrial fibrillation occurs suddenly, and many times can only be corrected by discharging electrical energy into the atria of the heart of the patient. This treatment is preferably synchronized to a detected R wave of the heart in order to avoid shocking the atria during the T wave or vulnerable period of the heart. The amount of energy which may be required to successfully cardiovert the atria can be as low as one joule and as high as six joules. In most cases, energy of about two to four joules is required to cardiovert atrial fibrillation back to normal sinus rhythm (NSR).

Implantable atrial defibrillators are known which detect the presence of atrial fibrillation and provide a single cardioverting pulse of electrical energy to the atria when atrial fibrillation is detected. Usually, the therapy is applied in synchrony with a detected R wave to avoid therapy application during the ventricular vulnerable period of the heart thereby preventing the induction of a lethal ventricular arrhythmia.

Atrial fibrillation detection may be initiated at spaced apart times with such devices to conserve battery power as disclosed, for example, in U.S. Pat. No. 5,464,432. Alternatively, such devices may provide continuous monitoring of heart activity to activate more specific atrial fibrillation detections when the monitored activity indicates a probability of atrial fibrillation.

One such atrial defibrillator is disclosed in U.S. Pat. No. 5,282,837. As disclosed in that patent, ventricular activity is continuously monitored. When the ventricular rate and/or ventricular rate variability reach a certain level, atrial fibrillation is suspected and a more robust and higher battery energy consumption algorithm for atrial fibrillation detection is initiated and implemented with a microprocessor.

Continuous monitoring of ventricular activity to predict when atrial fibrillation may be present may be effective for many patients. However, for patients with heart block, ventricular sensing may not be as effective as would be desirable. The reason for this is that when a patient has heart block, ventricular activity is generally not associated with or related to atrial activity. Hence, ventricular activity may not provide the best indication of possible atrial fibrillation.

In view of the foregoing, it would be desirable to be able to continuously monitor atrial activity for identifying possible atrial fibrillation. Such monitoring, would be effective for all patients, including heart block patients. However, atrial sensing for purely atrial events can be complicated by the presence of other heart activity, such as ventricular activity. Far field sensing of ventricular activations (R waves) could be mistaken for atrial activity resulting in false indications of possible atrial fibrillation. The present invention provides a system and method of detecting atrial events which avoids detection of R waves as atrial events to result in accurate predictions of possible atrial fibrillation.

SUMMARY OF THE INVENTION

The invention provides a system for detecting atrial events of a heart including A wave detecting means for detecting A waves of the heart and providing an A wave detection signal indicating each detected A wave. The A wave detecting means includes a first threshold and a second threshold higher than the first threshold. The system further includes an R wave detector for detecting R waves of the heart and which is coupled to the A wave detecting means for activating the second threshold of the A wave detecting means during each detected R wave of the heart.

The invention further provides a system for detecting atrial events of a heart including a first sense amplifier for sensing atrial activity of a heart and a second sense amplifier for sensing ventricular activity of the heart. The system further includes A wave detecting means coupled to the first sense amplifier for providing an output signal indicating each detected A wave. The A wave detecting means has a first threshold and a second threshold higher than the first threshold. An R wave detector is coupled to the second sense amplifier for detecting R waves from the sensed ventricular activity. Delay means causes a delay in the output signal and switch means coupled to the R wave detector switch the A wave detecting means from the first threshold to the second threshold during each detected R wave.

The present invention still further provides a continuous monitoring system for monitoring atrial activity of a heart and activating atrial fibrillation detection when atrial fibrillation is suspected. The system includes A wave detecting means for detecting A waves of the heart and providing an A wave detection signal indicating each detected A wave wherein the A wave detecting means includes a first threshold and a second threshold higher than the first threshold. The system further includes an R wave detector for detecting R waves of the heart and coupled to the A wave detecting means for activating the second threshold of the A wave detecting means during each detected R wave of the heart; means for determining an atrial cycle length from the A wave detection signal, and activation means for activating atrial fibrillation detection responsive to the atrial cycle lengths.

The invention still further provides a method of detecting atrial events of a heart. The method includes the steps of sensing atrial activity of the heart, sensing ventricular activity of the heart, detecting R waves from the sensed ventricular activity, and detecting A waves from the sensed atrial activity with a first threshold and with a second threshold higher than the first threshold during detected R waves.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole FIGURE of which like reference numerals identify identical elements, and wherein the sole FIGURE is a schematic block diagram of a fully implantable atrial defibrillator embodying the present invention.

DETAILED DESCRIPTION OF THE PREFERRED EMBODIMENT

Prior to referring to FIG. 1, a general description of a typical or normal cardiac cycle may be helpful in understanding the operation and various aspects of the present invention. The beginning of a cardiac cycle in normal sinus rhythm is initiated by a P wave which is normally a small positive wave. The P wave induces depolarization of the atria of the heart. Following the P wave there is a cardiac cycle portion which is substantially constant having a time duration on the order of, for example, 120 milliseconds. As a precaution, and to avoid potential confusion, the term "A wave" shall be used herein to denote atrial activity including P waves satisfying certain amplitude or threshold requirements.

The QRS complex of the cardiac cycle then normally occurs after the substantially constant portion. The dominating feature of the QRS complex is the ventricular activation, or R wave, which is a rapid positive or negative deflection. The R wave generally has an amplitude greater than any other wave of the cardiac cycle and is characterized by a rapid deviation from and return toward baseline. The R wave is the depolarization of the ventricles. The QRS complex is completed by the S wave which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds.

Referring now to FIG. 1, it illustrates a fully implantable atrial defibrillator 30 embodying the present invention shown in association with a schematically illustrated human heart 10. The portions of the heart 10 illustrated in the sole figure are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 27.

The atrial defibrillator 30 generally includes an enclosure 32 for hermetically sealing the internal circuit elements of the atrial defibrillator to be described hereinafter, a ventricular endocardial or first lead 34, a right atrial endocardial or second lead 35 and an intravascular or third lead 36. The enclosure 32 and leads 34, 35, and 36 are arranged to be implanted beneath the skin of a patient so as to render the atrial defibrillator 30 fully implantable.

The intravascular lead 36 generally includes a first or tip electrode 44 and a second proximal electrode 46. As illustrated, the lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. The electrodes 44 and 46 are preferably elongated cardioverting electrodes.

The first lead 34 preferably comprises a ventricular endocardial lead having bi-polar pair electrodes 38 and 40 arranged for establishing electrical contact with the right ventricle 12 of the heart 10. The electrodes 38 and 40 permit bi-polar sensing of ventricular activations in the right ventricle and pacing in the right ventricle. As illustrated, the lead 34 is fed through the superior vena cava 20, into the right atrium 16, and then into the right ventricle 12.

The second lead 35 preferably comprises a right atrial endocardial lead having bi-polar pair electrodes 37 and 39. Electrode 39 preferably is a helical screw-in coil for both providing fixation of the lead 35, as known in the art, and establishing electrical contact with the right atrium 16 of the heart 10. The electrodes 37 and 39 permit localized bi-polar sensing of heart activity in the right atrium. As illustrated, the lead 35 is fed through the superior vena cava 20 and into the right atrium 16.

Within the enclosure 32, the atrial defibrillator 30 includes a first sense amplifier 50, a second sense amplifier 51, a third sense amplifier 54 and an R wave detector 52. The first sense amplifier 50 forms an RV channel which provides an electrogram of the sensed right ventricular heart activity at an input of multiplexer 45 and to an input of an R wave detector 52.

The second sense amplifier 51 forms an RA channel to provide an electrogram of the sensed right atrial heart activity at its output which is coupled to an input of multiplexer 45 and to an input of a first A wave detector 53 and an input to a second A wave detector 55. The first and second A wave detectors 53 and 55 are in turn coupled to first and second delay circuits 57 and 59 respectively. The delay circuits 57 and 59 are coupled as inputs to a switch 61. As will be explained subsequently, the A wave detectors 53 and 55, delay circuits 57 and 59, and switch 61 form a system 41 for reliably detecting A waves in accordance with this embodiment of the present invention.

The third sense amplifier 54 forms an RACS channel to provide an electrogram of the sensed right atrium to left atrium heart activity at its output which is coupled to another input of the multiplexer 45. Each of the sense amplifiers 50, 51 and 54 may include a differentiating filter so that the electrograms which they provide are differentiated electrogram signals.

The R wave detector 52 provides one or more output pulses for each R wave sensed during a cardiac cycle of the heart. To that end, the R wave detector may include a further differentiating filter for differentiating the differentiated cardiac signal provided by sense amplifier 50 resulting in a twice differentiated second cardiac signal. The R wave detector 52 may further include a threshold circuit for setting an upper and lower threshold which provides an output when the twice differentiated second cardiac signal transitions beyond either the upper or lower thresholds.

Finally, the R wave detector preferably further includes an output pulse rate limiter (not shown) having a programmable pulse repetition time interval. The pulse repetition time interval is set to be as short as possible to allow detection of the last threshold crossing for an R wave. The R wave detector 52 thus provides at least one such pulse to indicate the beginning of each detected R wave and one such pulse to indicate the completion of each detected R wave so that the beginning and end of each R wave may be determined. The R wave detector 52 is coupled to the switch 61 for controlling the operation of the switch.

The A wave detectors 53 and 55 also preferably include a similar further differentiating filter (not shown) and output pulse rate limiter (not shown). This similarly enables the A wave detectors to provide at least one output pulse to indicate the beginning of each sensed A wave and another to indicate the end of each sensed A wave.

The enclosure 32 of the atrial defibrillator 30 further includes a microprocessor 62. The microprocessor 62 is preferably implemented in accordance with this embodiment of the present invention to result in a plurality of functional stages. The stages include an atrial arrhythmia detector in the form of an atrial fibrillation detector 70 and a charge and energy delivery control stage 74.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, in the memory at the addresses defined by multiple-bit addresses conveyed over the address bus 94 and conveys the operating parameters and data to the memory 90 over the multiple-bit data bus 96. During a read operation, the microprocessor 62 obtains data or operating parameters from the memory at the storage locations identified by the multiple-bit addresses provided over the address bus 94 and receives the operating parameters and data from the memory over the bi-directional data bus 96.

For entering operating parameters into the memory 90, the microprocessor 62 receives the programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or receives programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from the external controller 100 and for transmitting data to the external controller 100. One preferred communication system is disclosed in U.S. Pat. No. 5,342,408 which issued on Aug. 30, 1994 for "Telemetry System for an Implantable Cardiac Device," which patent is assigned to the assignee of the present invention and incorporated herein by reference.

The atrial defibrillator 30 further includes an analog to digital converter 47 and a direct memory access controller (DMA) 49. The analog to digital converter 47 has an input coupled to the output of the multiplexer 45 for receiving the electrogram signals generated by the sense amplifiers 50, 51, and 54. During a data acquisition, the analog to digital converter 47 converts the electrogram signals into digital data. The digital data is received by the DMA 49 which conveys the digital data to memory 90 over a data bus 49a for storage in memory at predetermined locations selected by the DMA 49 over an address bus 49b. The electrogram signals thus stored in digital form representing activity of the heart are thereafter utilized by the microprocessor to perform various functions. For example, for atrial fibrillation detection, the atrial fibrillation detector 70 utilizes the stored data from the RACS channel for detecting the presence of atrial fibrillation of the heart.

The atrial defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. The defibrillator 30 further includes a depletable power source 80, such as a lithium battery, for providing power to the electrical components of the atrial defibrillator 30, and a real time clock 82.

To briefly describe the operation of the atrial defibrillator for cardioverting atrial fibrillation of the heart, when an atrial fibrillation detection is initiated as described subsequently in accordance with the present invention, the sense amplifiers 50 and 54, the analog to digital converter 47, the multiplexer 45 and the DMA 49 are enabled. A data acquisition is first performed for a data acquisition period of, for example, eight seconds. During the eight second data acquisition period, the electrogram signals from sense amplifiers 50, 51, and 54 are digitized by the analog to digital converter 57 into digital data and the digital data is caused to be stored in the memory 90 by the DMA 49 as previously described.

After the eight second data acquisition period is completed, the atrial fibrillation detector 70 is enabled and analyzes the stored electrogram data from the RACS channel. The atrial fibrillation detector 70 may determine if the atria 16 and 18 are in fibrillation in a manner known in the art as, for example, described in U.S. Pat. No. 5,486,199 which issued on Jan. 13, 1996 for "System and Method For Reducing False Positives In Atrial Fibrillation Detection," which patent is assigned to the assignee of the present invention and incorporated herein by reference. If the atria are in fibrillation and thus in need of cardioversion, the charge delivery control 74 causes the charger and storage capacitor circuit 76 to charge the storage capacitor within the circuit 76 to a selected peak voltage. After the capacitor is charged, another data acquisition is performed and the atrial fibrillation detector 70 confirms the presence of atrial fibrillation. Thereafter, and in timed relation to a detected R wave, the discharge circuit 78, applies a portion of the stored electrical energy to electrodes 44 and 46 and thus the atria 16 and 18 to cardiovert the atria 16 and 18.

In accordance with a preferred embodiment of the present invention, an atrial fibrillation detection is initiated by the A wave detection system 41, an atrial cycle length (ACL) determining stage 64 and a comparator 66. The sense amplifier 51 continuously monitors and senses activity of the heart from the electrode pair 37, 39 in the right atrium. It thereby provides an atrial electrogram to the A wave detectors 53 and 55.

The first and second A wave detectors 53 and 55 are preferably identical except that the second A wave detector 55 has a threshold which is higher than the threshold of the first A wave detector 53. Hence, a higher amplitude electrogram signal is required to cause an A wave detection output from the second A wave detector 55 than is required to cause an A wave detection output from the first A wave detector 53. As will be seen hereinafter, A wave detection is normally performed by the first A wave detector 53 having the lower threshold.

The switch 61 switches between the delay circuits 57 and 59. Normally, switch 61 receives A wave detection outputs from the delay circuit 57.

The ACL stage 64 computes atrial cycle lengths, in a continuous manner, from the A wave detection output received from the switch 61. It provides the atrial cycle lengths to the comparator 66 which compares the computed atrial cycle lengths to a predetermined limit, such as 200 milliseconds, for example. When an atrial cycle length falls below the predetermined limit, the comparator activates or wakes up the microprocessor 62 to initiate an atrial fibrillation detection.

To avoid mistaking a far field sensed R wave for an A wave, during each detected R wave, the switch selects delay circuit 59. This causes the higher threshold of A wave detector 55 to be used for detecting A waves. Since far field sensed R waves should be lower in amplitude than actual A waves as sensed by electrodes 37 and 38, raising the detection threshold during R waves causes far field sensed R waves to be undetected. When each R wave is completed, the switch returns to select delay circuit 57. In this way, A wave detection is normally performed using the lower detection threshold of A wave detector 53 and with maximum sensitivity.

Because the RA sense amplifier 51 may sense an R wave before the RV sense amplifier 50, the delay circuits 57 and 59 are provided to introduce a short delay in the atrial detection signals. Because there is no delay in the electrogram from the RV sense amplifier 50 or detected R waves from R wave detector 52 to the switch 61, it will be assured that the A wave detection threshold will be raised before an R wave has an opportunity of being considered an A wave.

As those skilled in the art will appreciate, the delay may alternatively be introduced at the output of sense amplifier 51. Further, if the delay were introduced in this alternative manner, a single A wave detector having selective lower and higher thresholds may be employed with the threshold selection being performed by the R wave detector as described.

While particular embodiments of the present invention have been shown and described, modifications may be made, and it is therefore intended in the appended claims to cover all such changes and modifications which fall within the true spirit and scope of the invention.

What is claimed is:

1. A system for detecting atrial events of a heart comprising:

A wave detecting means for detecting A waves of the heart and providing an A wave detection signal indicating each detected A wave, the A wave detecting means including a first threshold and means for providing the A wave detection signal when an A wave is detected with the first threshold and a second threshold higher than the first threshold and means for providing the A wave detection signal when an A wave is detected with the second threshold; and an R wave detector for detecting R waves of the heart and coupled to the A wave detecting means for activating the second threshold of the A wave detecting means during each detected R wave of the heart.

2. A system as defined in claim 1 further including delay means for delaying the A wave detection signal.

3. A system as defined in claim 1 wherein the system further includes an atrial sense amplifier for sensing atrial activity of the heart and providing an electrogram signal and wherein the A wave detecting means include first and second A wave detectors each having an output and an input coupled to the atrial sense amplifier for receiving the electrogram signal, first and second delay circuits each having an output and an input coupled to the first and second A wave detector outputs respectively, a switch having an output for providing the A wave detection signal and being selectively coupled to the first and second delay circuit outputs responsive to the R wave detector.

4. A system for detecting atrial events of a heart comprising:

a first sense amplifier for sensing atrial activity of a heart;

a second sense amplifier for sensing ventricular activity of the heart;

A wave detecting means coupled to the first sense amplifier for providing an output signal indicating each detected A wave, said A wave detecting means having a first threshold and means for providing the output signal when an A wave is detected with the first threshold and a second threshold higher than the first threshold and means for providing the output signal when an A wave is detected with the second threshold;

an R wave detector coupled to the second sense amplifier for detecting R waves from the sensed ventricular activity;

delay means for causing a delay in the output signal; and switch means coupled to the R wave detector for switching the A wave detecting means from the first threshold to the second threshold during each detected R wave.

5. A continuous monitoring system for monitoring atrial activity of a heart and activating atrial fibrillation detection when atrial fibrillation is suspected, the system comprising:

A wave detecting means for detecting A waves of the heart and providing an A wave detection signal indicating each detected A wave, the A wave detecting means including a first threshold and means for providing the A wave detection signal when an A wave is detected with the first threshold and a second threshold higher than the first threshold and means for providing the A wave detection signal when an A wave is detected with the second threshold;

an R wave detector for detecting R waves of the heart and coupled to the A wave detecting means for activating the second threshold of the A wave detecting means during each detected R wave of the heart;

means for determining an atrial cycle length from the A wave detection signal; and activation means for activating atrial fibrillation detection responsive to the atrial cycle lengths.

6. A system as defined in claim 5 further including delay means for delaying the A wave detection signal.

7. A system as defined in claim 5 wherein the activation means comprises a comparator.

8. A system as defined in claim 5 wherein the system further includes an atrial sense amplifier for sensing atrial activity of the heart and providing an electrogram signal and wherein the A wave detecting means includes first and second A wave detectors each having an output and an input coupled to the atrial sense amplifier for receiving the electrogram signal, first and second delay circuits each having an output and an input coupled to the first and second A wave detector outputs respectively, a switch having an output for providing the A wave detection signal and being selectively coupled to the first and second delay circuit outputs responsive to the R wave detector.

9. A method of detecting atrial events of a heart, the method including the steps of:

sensing atrial activity of the heart;

sensing ventricular activity of the heart;

detecting R waves from the sensed ventricular activity; and detecting A waves from the sensed atrial activity with a first threshold and detecting A waves from the sensed atrial activity with a second threshold higher than the first threshold during detected R waves.

* * * * *